US010034612B2

(12) United States Patent
Shimuta et al.

(10) Patent No.: US 10,034,612 B2
(45) Date of Patent: Jul. 31, 2018

(54) BIOLOGICAL STATE ELIMINATING APPARATUS AND METHOD

(71) Applicants:Murata Manufacturing Co., Ltd., Nagaokakyo-shi, Kyoto-fu (JP); FATIGUE SCIENCE LABORATORY INC., Osaka-shi, Osaka (JP)

(72) Inventors: Toru Shimuta, Nagaokakyo (JP); Hirohiko Kuratsune, Nagaokakyo (JP); Yasuyoshi Watanabe, Nagaokakyo (JP)

(73) Assignees: MURATA MANUFACTURING CO., LTD., Nagaokakyo-Shi, Kyoto-Fu (JP); FATIGUE SCIENCE LABORATORY INC., Osaka-Shi, Osaka (JP)

( * ) Notice: Subject to any disclaimer, the term of this patent is extended or adjusted under 35 U.S.C. 154(b) by 0 days.

(21) Appl. No.: 14/978,502

(22) Filed: Dec. 22, 2015

(65) Prior Publication Data

US 2016/0106320 A1 Apr. 21, 2016

Related U.S. Application Data

(63) Continuation of application No. PCT/JP2014/064692, filed on Jun. 3, 2014.

(30) Foreign Application Priority Data

Jun. 28, 2013 (JP) .................................. 2013-136472

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02125* (2013.01); *A61B 5/02416* (2013.01);
(Continued)

(58) Field of Classification Search
CPC . A61B 5/02416; A61B 5/7246; A61B 5/0205; A61B 5/02427; A61B 5/0004;
(Continued)

(56) References Cited

U.S. PATENT DOCUMENTS 8,147,416 B2 * 4/2012 Fayram ................ A61B 5/0215
600/481
8,162,841 B2 * 4/2012 Keel ................... A61B 5/02158
600/481
(Continued)

FOREIGN PATENT DOCUMENTS

CN 102811659 A 12/2012
JP H08-71047 A 3/1996
(Continued)

OTHER PUBLICATIONS

International Search Report issued for PCT/JP2014-064692, dated Aug. 12, 2014.
(Continued)

*Primary Examiner* — Deborah Malamud
(74) *Attorney, Agent, or Firm* — Arent Fox LLP

(57) ABSTRACT

A biological state estimating apparatus includes a pair of electrocardiographic electrodes, a photoplethysmographic sensor, and a controller that includes a peak detecting section, a pulse transmission time measuring section, a correlation information storing section, and a biological state estimating section. The electrocardiographic electrodes detect an electrocardiogram signal and the photoplethysmographic sensor, which has light-emitting and light-receiving elements, detects a photoplethysmogram signal. The controller detects peaks of the electrocardiogram and photoplethysmogram signals and determines a pulse transmission time from the time difference between the respective peaks of the photoplethysmogram and the electrocardiogram signal. Memory stores information determined in advance
(Continued)

based on the relationship between pulse transmission time and biological state. The controller further estimates the biological state of the user on the basis of the pulse transmission time, and the correlation information stored in the correlation information storing section.

15 Claims, 11 Drawing Sheets

(51) Int. Cl.
*A61B 5/0408* (2006.01)
*A61B 5/0452* (2006.01)
*A61B 5/16* (2006.01)
*A61B 5/021* (2006.01)
*A61B 5/0456* (2006.01)
*A61B 5/024* (2006.01)
*A61B 5/1455* (2006.01)

(52) U.S. Cl.
CPC .......... *A61B 5/0452* (2013.01); *A61B 5/0456* (2013.01); *A61B 5/04085* (2013.01); *A61B 5/165* (2013.01); *A61B 5/7246* (2013.01); *A61B 5/02438* (2013.01); *A61B 5/14551* (2013.01); *A61B 5/4035* (2013.01); *A61B 2560/0431* (2013.01)

(58) Field of Classification Search
CPC ..... A61B 5/0402; A61B 5/0059; A61B 5/024; A61B 5/0245; A61B 5/02444; A61B 5/0295; A61B 5/0806; A61B 5/72; A61B 2562/06; Y10S 323/911
See application file for complete search history.

(56) References Cited

U.S. PATENT DOCUMENTS

| | | |
|---|---|---|
| 8,602,997 B2 | 12/2013 | Banet et al. |
| 2003/0078508 A1 | 4/2003 | Nakagawa |
| 2005/0217674 A1 | 10/2005 | Burton et al. |
| 2006/0200011 A1 | 9/2006 | Suzuki et al. |
| 2007/0276632 A1 | 11/2007 | Banet et al. |
| 2008/0249382 A1 | 10/2008 | Oh et al. |
| 2009/0240119 A1* | 9/2009 | Schwaibold ............ A61B 5/00 600/301 |
| 2010/0160798 A1 | 6/2010 | Banet et al. |

FOREIGN PATENT DOCUMENTS

| | | |
|---|---|---|
| JP | H11-299740 A | 11/1999 |
| JP | 2002-238867 A | 8/2002 |
| JP | 2003-126053 A | 5/2003 |
| JP | 2003-290164 A | 10/2003 |
| JP | 2006-518100 A | 6/2006 |
| JP | 2006-212218 A | 8/2006 |
| JP | 2010-051822 A | 3/2010 |
| JP | 2012-139342 A | 7/2012 |
| JP | 5080550 B2 | 11/2012 |
| JP | 2013-022211 A | 2/2013 |
| WO | WO 2011082431 A1 | 7/2011 |

OTHER PUBLICATIONS

Written Opinion of the International Searching Authority issued for PCT/JP2014/064692, dated Aug. 12, 2014.

* cited by examiner

BIOLOGICAL STATE ELIMINATING APPARATUS AND METHOD

CROSS-REFERENCE TO RELATED APPLICATIONS

The present application is a continuation of PCT/JP2014/064692 filed Jun. 3, 2014, which claims priority to Japanese Patent Application No. 2013-136472, filed Jun. 28, 2013, the entire contents of each of which are incorporated herein by reference.

FIELD OF THE INVENTION

The present invention relates to a biological state estimating apparatus and method that estimates the biological state of a human.

BACKGROUND OF THE INVENTION

It is common to evaluate autonomic function on the basis of the results of frequency analysis (spectral analysis) of heart rate variability (variation of R-R interval) on an electrocardiogram (ECG) by using fast Fourier transform and other techniques. It is known that low frequency components (LF) up to 0.15 Hz contained in the frequency analysis results of heart rate variability predominantly reflect sympathetic function (partially including parasympathetic function), while high frequency components (HF) equal to or higher than 0.15 Hz contained in the frequency analysis results reflect parasympathetic function. The ratio (LF/HF) between the low frequency components and the high frequency components is used as an index of autonomic function.

Patent Document 1 discloses an autonomic function evaluating apparatus described below. To evaluate autonomic function and other information, this autonomic function evaluating apparatus uses an acceleration plethysmogram (APG) signal, which is obtained by taking the second derivative of a photoplethysmogram (PPG) signal, instead of an electrocardiogram signal. The autonomic function evaluating apparatus computes an acceleration plethysmogram by taking the second derivative of the waveform of a plethysmogram measured continuously over a predetermined period of time. From the obtained waveform of the acceleration plethysmogram, the autonomic function evaluating apparatus then determines variation of the a-a interval (interpulse interval) corresponding to variation of the R-R interval on an electrocardiogram. Subsequently, the autonomic function evaluating apparatus performs frequency analysis of the temporal variation of the a-a interval, and uses the results to evaluate autonomic function.

The autonomic function evaluating apparatus allows autonomic function to be evaluated by measuring the plethysmogram of the fingertip of a person in a seated position using a photoplethysmographic sensor. This eliminates the need for, for example, removal of clothing or attachment of a plurality of electrocardiographic electrodes to take a measurement, allowing the evaluation results to be obtained with greater ease compared to those obtained using an electrocardiogram.

Patent Document 1: Japanese Patent No. 5080550.

The above conventional approaches to evaluate autonomic function by heart rate variability analysis (frequency analysis) using data such as an electrocardiogram and an acceleration plethysmogram require data such as heart rate to be taken under stable conditions of the autonomic nervous system (that is, the sympathetic and parasympathetic nervous systems). This requires the user (subject) to relax in a resting seated position for about five minutes, for example, prior to taking a measurement. After taking sufficient rest, the user is then required to have his or her electrocardiogram or photoplethysmogram continuously measured in that state for the duration of, for example, three minutes or more (or, for example, one hundred beats or more).

Consequently, the conventional heart rate variability analysis may fail to correctly evaluate autonomic function in situations where the sympathetic nerve becomes dominant, such as when the subject is not allowed sufficient rest prior to measurement or when the subject is unable to remain at rest during measurement. For conventional autonomic function analysis, data such as the amount of autonomic activity (TP) or autonomic balance (LF/HF) measured after rest is known to be associated with, for example, the subjective symptoms of fatigue, the amount of activity during wakefulness, and sleep efficiency. Unfortunately, the association between autonomic function and these pieces of information is lost if a measurement is taken immediately without giving the subject a five-minute rest, seriously undermining the diagnostic value of such an autonomic function analysis. This has led to a desire for a technique that, in acquiring biological information including an electrocardiogram and a photoplethysmogram (acceleration plethysmogram), allows a biological state such as autonomic function to be estimated in a shorter time without requiring the user (subject) to remain at rest.

SUMMARY OF THE INVENTION

The present invention has been made to address the problems mentioned above. Accordingly, it is an object of the invention to provide a biological state estimating apparatus and method that, in acquiring biological information to estimate biological state, allows the biological state to be estimated in a shorter time without requiring the user to remain at rest.

A biological state estimating apparatus according to the present invention includes a pair of electrocardiographic electrodes that detects an electrocardiogram signal, a photoplethysmographic sensor that detects a photoplethysmogram signal, the photoplethysmographic sensor having a light-emitting element and a light-receiving element, peak detecting means for detecting a peak of the electrocardiogram signal detected by the electrocardiographic electrodes, and a peak of the photoplethysmogram signal detected by the photoplethysmographic sensor, pulse transmission time calculating means for calculating a pulse transmission time from a time difference between the peak of the photoplethysmogram signal and the peak of the electrocardiogram signal which are detected by the peak detecting means, correlation information storing means for storing correlation information, the correlation information being determined in advance on a basis of a relationship between pulse transmission time and biological state, and biological state estimating means for estimating a biological state of a user, on a basis of the pulse transmission time calculated by the pulse transmission time calculating means and the correlation information stored in the correlation information storing means.

With the biological state estimating apparatus according to the present invention, the correlation information indicating the relationship between pulse transmission time and biological information is acquired and stored in advance, and the user's biological state is estimated on the basis of the pulse transmission time calculated from the time difference between the peak of the electrocardiogram signal and the peak of the photoplethysmogram signal, and the stored correlation information. That is, pulse transmission time calculated from the time difference between the peak of the electrocardiogram signal and the peak of the photoplethysmogram signal is used as an index of biological state. Pulse transmission time has a correlation with, for example, mental fatigue and post-rest LF/HF (details in this regard will be given later). That is, a correlation is observed between pulse transmission time and, for example, the degree of fatigue or autonomic function. Further, the detected pulse transmission time varies little between when measured at rest and when measured without resting. That is, using pulse transmission time as an index eliminates the need for the user to remain at rest prior to and during the measurement (a detailed description in this regard will be given later). Data for estimating biological state may be collected for any length of time that is sufficient to obtain pulse transmission time. Hence, in theory, the duration of one beat is sufficient to estimate biological state. Consequently, the measurement time required for biological state evaluation can be shortened in comparison to conventional methods using frequency analysis. As a result, in acquiring biological information for estimating biological state, the user is not required to remain at rest, and further, the biological state of the user can be estimated in a shorter time.

Depending on the case, the term pulse transmission time refers to either the time taken for a pulse wave to travel between two predetermined sites in a living body, or the time difference between the peak of an electrocardiogram signal and the peak of a plethysmogram signal. As used herein, the term pulse transmission time has the latter meaning.

Preferably, in the biological state estimating apparatus according to the present invention, the correlation information storing means stores fatigue correlation information, the fatigue correlation information being determined in advance on a basis of a relationship between pulse transmission time and degree of fatigue, and the biological state estimating means estimates a degree of fatigue of the user, on a basis of the pulse transmission time and the fatigue correlation information.

In this case, the fatigue correlation information is stored, which is determined in advance on the basis of the relationship between pulse transmission time and degree of fatigue. Thus, by measuring the pulse transmission time of the user and using the measured pulse transmission time as an index, the degree of fatigue can be estimated and evaluated as a biological state.

Preferably, in the biological state estimating apparatus according to the present invention, the correlation information storing means stores autonomic function correlation information, the autonomic function correlation information being determined in advance on a basis of a relationship between pulse transmission time and autonomic function, and the biological state estimating means estimates autonomic function of the user, on a basis of the pulse transmission time and the autonomic function correlation information.

In this case, the autonomic function correlation information is stored, which is determined in advance on the basis of the relationship between pulse transmission time and autonomic function. Thus, by measuring the pulse transmission time of the user and using the measured pulse transmission time as an index, autonomic function can be estimated and evaluated as a biological state. LF/HF after resting and autonomic function have correlation. Consequently, pulse transmission time and autonomic function have correlation.

Preferably, the biological state estimating apparatus according to the present invention further includes pulse transmission time storing means for storing the pulse transmission time calculated by the pulse transmission time calculating means, the correlation information storing means stores sleep state correlation information, the sleep state correlation information being determined in advance on a basis of a relationship between pulse transmission time before sleep, pulse transmission time after sleep, and state of sleep, and the biological state estimating means estimates a state of sleep of the user, on a basis of the pulse transmission time before sleep calculated by the pulse transmission time calculating means and stored in the pulse transmission time storing means, the pulse transmission time after sleep calculated by the pulse transmission time calculating means, and the sleep state correlation information.

In this case, the sleep state correlation information is stored, which is determined in advance on the basis of the relationship between pulse transmission time before and after sleep and state of sleep. Thus, by measuring the pulse transmission time of the user before and after sleep and using the measured pulse transmission time as an index, the state of sleep (the quality of sleep, that is, the degree of recovery from fatigue) can be estimated and evaluated as a biological state.

Preferably, the biological state estimating apparatus according to the present invention further includes pulse transmission time storing means for storing variation of the pulse transmission time calculated by the pulse transmission time calculating means, the correlation information storing means stores sleep state correlation information, the sleep state correlation information being determined in advance on a basis of a relationship between variation of pulse transmission time during sleep and state of sleep, and the biological state estimating means estimates a state of sleep of the user, on a basis of the variation of the pulse transmission time during sleep stored in the pulse transmission time storing means, and the sleep state correlation information.

In this case, the sleep state correlation information is stored, which is determined in advance on the basis of the relationship between variation of pulse transmission time during sleep and state of sleep. Thus, by measuring the variation of pulse transmission time of the user during sleep, the state of sleep (the quality of sleep, that is, the degree of recovery from fatigue) can be estimated and evaluated.

Preferably, the biological state estimating apparatus according to the present invention further includes variation calculating means for calculating an amount of variation in pulse transmission time before and after a predetermined action that places a load on a heart, the correlation information storing means stores blood vessel distensibility correlation information, the blood vessel distensibility correlation information being determined in advance on a basis of a relationship between amount of variation in pulse transmission time before and after the predetermined action, and blood vessel distensibility, and the biological state estimating means estimates blood vessel distensibility of the user, on a basis of the amount of variation in pulse transmission time calculated by the variation calculating means, and the blood vessel distensibility correlation information.

The biological state estimating apparatus according to the present invention stores the blood vessel distensibility correlation information, which is determined in advance on the basis of the relationship between amount of variation in pulse transmission time before and after a predetermined action, and distensibility of the blood vessel. Thus, by measuring the pulse transmission time of the user, the distensibility of the blood vessel can be estimated and evaluated as a biological state by using the amount of variation in pulse transmission time as an index.

Preferably, in the biological state estimating apparatus according to the present invention, the electrocardiographic electrodes are attached to an identical housing, in such a location that when the user grasps the housing with left and right hands, one of the left and right hands is in contact with one of the electrocardiographic electrodes, and another one of the left and right hands is in contact with another one of the electrocardiographic electrodes, and the photoplethysmographic sensor is attached to the housing, in such a location that when the user grasps the housing with the left and right hands, the photoplethysmographic sensor is in contact with one of the left and right hands.

In this way, grasping the housing allows acquisition of an electrocardiogram signal between both hands, and a photoplethysmogram signal of one hand, that is, acquisition of pulse transmission time. Thus, the biological state can be estimated and evaluated by the user's simple action of grasping the housing.

Preferably, in the biological state estimating apparatus according to the present invention, one of the electrocardiographic electrodes is attached in contact with a site between a fingertip and a shoulder on one arm, another one of the electrocardiographic electrodes is attached in contact with a site between a fingertip and a shoulder on another arm, and a wiring cable connected to the electrocardiographic electrodes is routed along a surface of a body of the user, and the photoplethysmographic sensor is attached in contact with a site between a fingertip and a shoulder on one arm.

This allows pulse transmission time to be measured with the pair of electrocardiographic electrodes and the photoplethysmographic sensor placed on the body of the user. Thus, for example, as the user sleeps while wearing these components on the body, pulse transmission time during sleep is acquired to enable estimation/evaluation of the biological state (for example, the state of sleep). It is also possible to measure pulse transmission time during active daytime hours to sequentially estimate/evaluate the biological state (for example, the degree of fatigue).

Preferably, in the biological state estimating apparatus according to the present invention, the correlation information storing means stores the correlation information indicative of the relationship between pulse transmission time and biological information, individually for each age and/or each sex.

In this case, the correlation information indicating the relationship between pulse transmission time and biological information is acquired and stored individually for, for example, each age or each sex. This allows for more accurate estimation/evaluation of biological state by taking differences due to, for example, age or sex into account.

Preferably, in the biological state estimating apparatus according to the present invention, the biological state estimating means automatically starts the estimating of the biological state of the user, upon satisfaction of at least one of conditions including detection of contact of the user with the biological state estimating apparatus, acquisition of the electrocardiogram signal and the photoplethysmogram signal over a predetermined number of beats, and payment of a consideration.

In this case, estimation of biological state is automatically started, eliminating the need for an action to start measurement/detection. This eliminates body motion noise resulting from such a starting action, and enables measurement/detection under relative resting conditions.

Preferably, in the biological state estimating apparatus according to the present invention, the biological state estimating means automatically ends estimation of the biological state of the user, upon acquisition of the electrocardiogram signal and the photoplethysmogram signal over a predetermined number of beats, and/or upon elapse of a predetermined time after the estimating of the biological state is started.

In this case, pulse transmission time measurement/biological state estimation is automatically ended upon its completion. This enables easier measurement of pulse transmission time to estimate biological state.

Preferably, the biological state estimating apparatus according to the present invention further includes presenting means for presenting guidance by voice and/or an image, at a time of automatically starting the estimating of the biological state and/or automatically ending the estimating of the biological state.

This makes it possible to inform the user of the status of measurement, such as start of measurement/estimation or end of measurement/estimation.

According to the present invention, in acquiring biological information to estimate biological state, the user is not required to remain at rest, and further, the biological state of the user can be estimated in a shorter time.

DETAILED DESCRIPTION

Hereinafter, preferred embodiments of the present invention will be described in detail with reference to the figures.

In the figures, the same elements are denoted by the same reference signs to avoid repetitive description.

Figure 1:
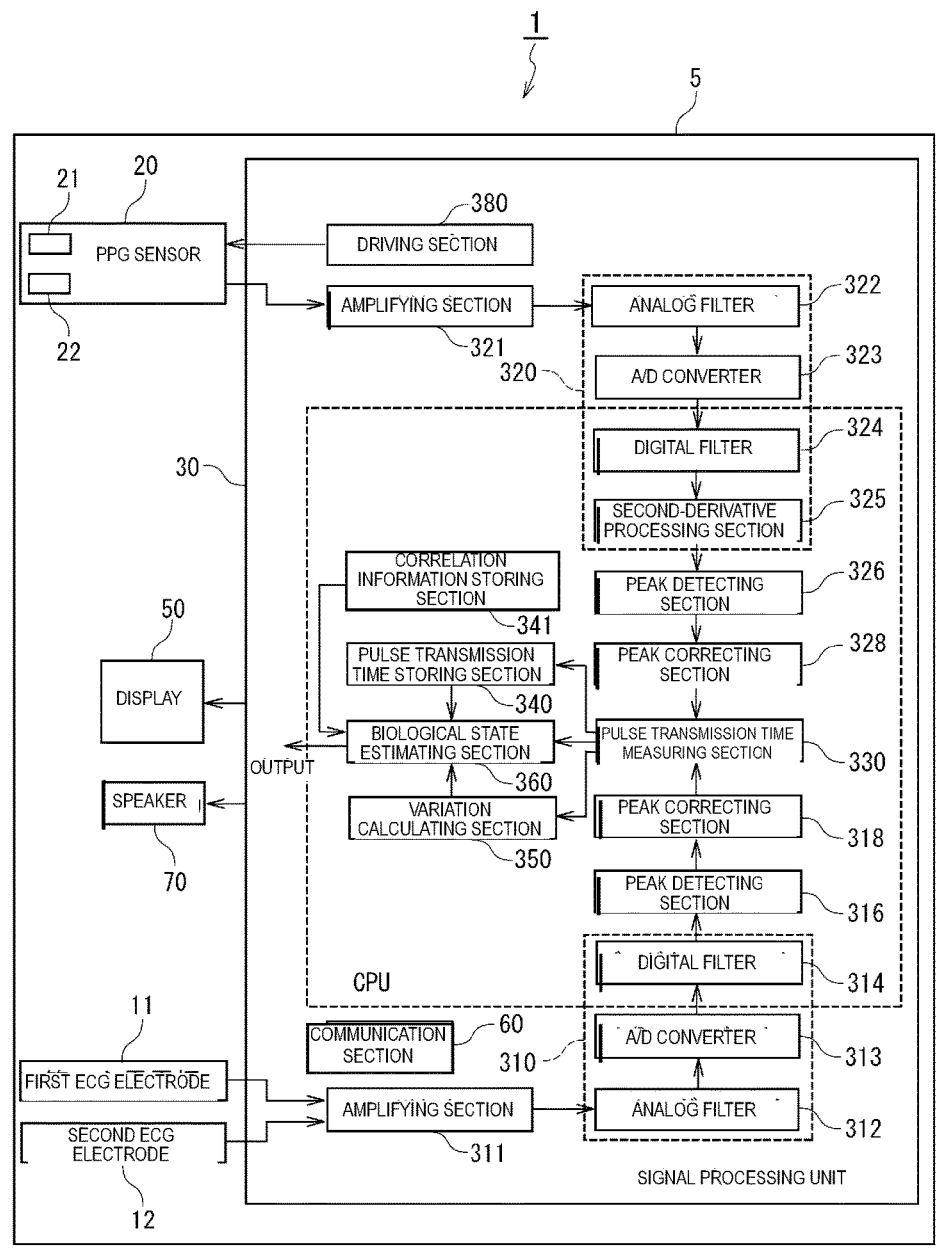
FIG. 1 is a block diagram illustrating a configuration of a biological state estimating apparatus according to an embodiment.
Figure 2:
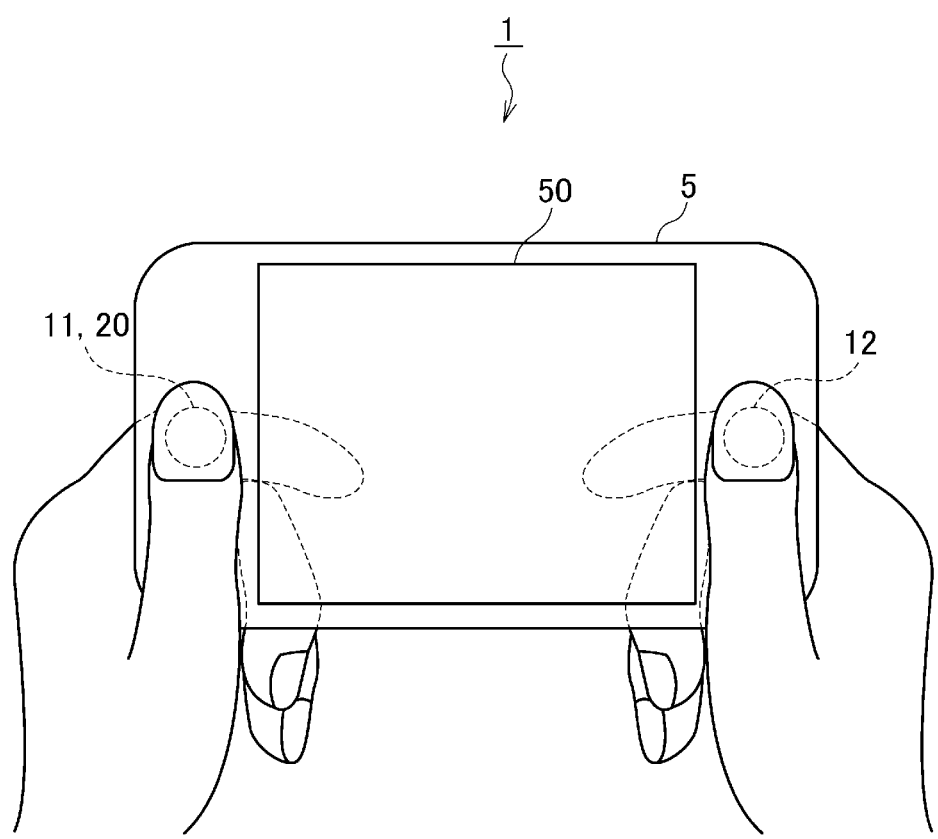
FIG. 2 illustrates the outward appearance of a biological state estimating apparatus according to an embodiment, and an example of how the biological state estimating apparatus is used.

First, a configuration of a biological state estimating apparatus 1 according to an embodiment will be described with reference to FIGS. 1 and 2. FIG. 1 is a block diagram illustrating a configuration of the biological state estimating apparatus 1. FIG. 2 illustrates the outward appearance of the biological state estimating apparatus 1, and an example of how the biological state estimating apparatus 1 is used.

The biological state estimating apparatus 1 detects an electrocardiogram signal and a photoplethysmogram signal, and measures pulse transmission time from the time difference between the R-wave peak of the detected electrocardiogram signal (electrocardiogram wave) and the peak (rising edge) of the detected photoplethysmogram signal (plethysmogram wave). Then, the biological state estimating apparatus 1 estimates the biological state (for example, the degree of fatigue, autonomic function, the quality of sleep, or the distensibility of the blood vessel) of the user on the basis of the measured pulse transmission time.

To this end, the biological state estimating apparatus 1 includes a pair of electrocardiographic electrodes (a first electrocardiographic electrode 11 and a second electrocardiographic electrode 12) for detecting an electrocardiogram signal, a photoplethysmographic sensor 20 for detecting a photoplethysmogram signal, and a signal processing unit 30 that measures, for example, pulse transmission time on the basis of the detected electrocardiogram signal and the detected photoplethysmogram signal to estimate the biological state. Hereinafter, these individual components will be described in detail.

The first electrocardiographic electrode 11 and the second electrocardiographic electrode 12 are used to detect an electrocardiogram signal. As illustrated in FIG. 2, the first electrocardiographic electrode 11 and the second electrocardiographic electrode 12 are respectively attached to the left-hand and right-hand surfaces of a housing 5 of the biological state estimating apparatus 1 in such a way that the first electrocardiographic electrode 11 and the second electrocardiographic electrode 12 each come into contact with the user's thumb when the user grasps the housing 5 with both hands. That is, when the user grasps the housing 5 (the biological state estimating apparatus 1) with both hands, the left and right hands (thumbs) of the user respectively come into contact with the first electrocardiographic electrode 11 and the second electrocardiographic electrode 12, thus acquiring an electrocardiogram signal corresponding to the difference in potential between the left and right hands of the user. Suitable examples of the material of the first electrocardiographic electrode 11 and the second electrocardiographic electrode 12 include metal (preferably a metal with high corrosion resistance and relatively low risk of causing metal allergy, such as stainless or Au), electrically conductive gel, electrically conductive rubber, and electrically conductive cloth. Other example of the metal of the first electrocardiographic electrode 11 and the second electrocardiographic electrode 12 include electrically conductive plastic and a capacitively coupled material. The first electrocardiographic electrode 11 and the second electrocardiographic electrode 12, which are connected to the signal processing unit 30 through a wiring cable, each output an electrocardiogram signal to the signal processing unit 30 by using the wiring cable.

The photoplethysmographic sensor 20 optically detects a photoplethysmogram signal by exploiting the light-absorption characteristics of hemoglobin in the blood. Accordingly, the photoplethysmographic sensor 20 includes a light-emitting element 21 and a light-receiving element 22. The photoplethysmographic sensor 20, which detects a photoplethysmogram signal, is disposed near (for example, arranged beside or integrated with) the electrocardiographic electrode 11. That is, the pair of first and second electrocardiographic electrodes 11 and 12, and the photoplethysmographic sensor 20 are attached to the same housing 5, in such locations that when the user grasps the housing 5 with the left and right hands, one of the hands (for example, the left hand) is in contact with the first electrocardiographic electrode 11 and the photoplethysmographic sensor 20, and the other hand (for example, the right hand) is in contact with the second electrocardiographic electrode 12.

The light-emitting element 21 emits light in response to a pulsed drive signal output from a driving section 380 of the signal processing unit 30. As the light-emitting element 21, for example, an LED, a Vertical Cavity Surface Emitting LASER (VCSEL), or a resonant type LED may be used. The driving section 380 generates and outputs a pulsed drive signal for driving the light-emitting element 21.

The light-receiving element 22 outputs a detection signal corresponding to the intensity with which light emitted from the light-emitting element 21 is incident on the light-receiving element 22 after passing through the human body, for example, the fingertip, or after being reflected by the human body. As the light-receiving element 22, for example, a photodiode or a phototransistor is suitable used. In the embodiment, a photodiode is used as the light-receiving element 22. The light-receiving element 22 is connected to the signal processing unit 30. A detection signal (photoplethysmogram signal) obtained by the light-receiving element 22 is output to the signal processing unit 30.

As described above, the first electrocardiographic electrode 11, the second electrocardiographic electrode 12, and the photoplethysmographic sensor 20 are each connected to the signal processing unit 30. Thus, a detected electrocardiogram signal and a detected photoplethysmogram signal are input to the signal processing unit 30.

The signal processing unit 30 processes an input electrocardiogram signal to measure, for example, heart rate and interbeat interval. The signal processing unit 30 also processes an input photoplethysmogram signal to measure, for example, pulse rate and interpulse interval. Further, the signal processing unit 30 measures, for example, pulse transmission time from the time difference between the R-wave peak of a detected electrocardiogram signal (electrocardiogram wave) and the peak (rising edge) of a detected photoplethysmogram signal (photoplethysmogram wave) (see FIG. 3). At this time, the signal processing unit 30 corrects a shift (delay) of the peak in each of a first signal processing section 310 and a second signal processing section 320 described later, and thus measures pulse transmission time with high accuracy. Then, the signal processing unit 30 estimates the user's biological state on the basis of the measured pulse transmission time, and correlation information that defines the relationship between pulse transmission time and biological state.

Accordingly, the signal processing unit 30 has amplifying sections 311 and 321, the first signal processing section 310, the second signal processing section 320, peak detecting sections 316 and 326, and peak correcting sections 318 and 328, as well as a pulse transmission time measuring section 330, a pulse transmission time storing section 340, a correlation information storing section 341, a variation calculating section 350, and a biological state estimating section 360. The first signal processing section 310 has an analog filter 312, an A/D converter 313, and a digital filter 314. The second signal processing section 320 has an analog filter 322, an A/D converter 323, a digital filter 324, and a second-derivative processing section 325.

Of the various components mentioned above, the digital filters 314 and 324, the second-derivative processing section 325, the peak detecting sections 316 and 326, the peak correcting sections 318 and 328, the pulse transmission time measuring section 330, the variation calculating section 350, and the biological state estimating section 360 are implemented by, for example, a CPU or controller that performs arithmetic processing described herein with respect to the various "sections", a ROM that stores a program and data for causing the CPU to execute various processes, and a RAM that temporarily stores various data such as computational results. That is, the functions of the various components mentioned above are implemented by execution of a program stored in the ROM by the CPU.

The amplifying section 311 is implemented by, for example, an amplifier such as an operational amplifier. The amplifying section 311 amplifies an electrocardiogram signal detected by the first electrocardiographic electrode 11 and the second electrocardiographic electrode 12. The electrocardiogram signal amplified by the amplifying section 311 is output to the first signal processing section 310. Likewise, the amplifying section 321 is implemented by, for example, an amplifier such as an operational amplifier. The amplifying section 321 amplifies a photoplethysmogram signal detected by the photoplethysmographic sensor 20. The photoplethysmogram signal amplified by the amplifying section 321 is output to the second signal processing section 320.

As described above, the first signal processing section 310 has the analog filter 312, the A/D converter 313, and the digital filter 314. The first signal processing section 310 applies filtering to the electrocardiogram signal amplified by the amplifying section 311 to extract pulsatile components from the electrocardiogram signal.

As described above, the second signal processing section 320 has the analog filter 322, the A/D converter 323, the digital filter 324, and the second-derivative processing section 325. The second signal processing section 320 applies filtering and second-order differentiation to the photoplethysmogram signal amplified by the amplifying section 321 to extract pulsatile components from the electrocardiogram signal.

The analog filter 312 or 322 and the digital filter 314 or 324 perform a filtering process aimed at improving S/N by removing those components (noise) other than frequencies that characterize an electrocardiogram signal or a photoplethysmogram signal. The above filtering process is described in more detail below. Generally, the dominant frequency components of an electrocardiogram signal are those in the range of 0.1 to 200 Hz, and the dominant frequency components of a photoplethysmogram signal are those in the vicinity of 0.1 to several tens Hz. Accordingly, for improved S/N, filtering is applied by using an analog filter and a digital filter such as a low pass filter and a band pass filter to pass only those portions of the corresponding signal in the above frequency range.

If the filtering is only aimed at extraction of pulsatile components (that is, if it is not required to acquire an electrocardiogram waveform, for example), the passband of frequencies may be narrowed to cut off components other than pulsatile components to improve noise resistance. Both of the analog filter 312 or 322 and the digital filter 314 or 324 may not necessarily be provided. Only one of the analog filter 312 or 322 and the digital filter 314 or 324 may be provided. The electrocardiogram signal that has undergone filtering by the analog filter 312 and the digital filter 314 is output to the peak detecting section 316. Likewise, the photoplethysmogram signal that has undergone second derivative by the analog filter 322 and the digital filter 324 is output to the second-derivative processing section 325.

The second-derivative processing section 325 takes the second derivative of a photoplethysmogram signal to acquire a second derivative plethysmogram (acceleration plethysmogram) signal. The acquired acceleration plethysmogram signal is output to the peak detecting section 326. Peaks (rising edges) on a photoplethysmogram are often not clearly defined and hence difficult to identify. Although this makes it desirable to convert a photoplethysmogram into an acceleration plethysmogram for peak detection, the second-derivative processing section 325 may not necessarily be provided.

The peak detecting section 316 detects the peak (R-wave) of an electrocardiogram signal to which signal processing has been applied (from which pulsatile components have been extracted) by the first signal processing section 310.

The peak detecting section 326 that is part of the controller detects the peak (rising edge) of a photoplethysmogram signal (acceleration plethysmogram) to which signal processing has been applied by the second signal processing section 320. That is, the peak detecting sections 316 and 326 function as peak detecting means. The peak detecting section 316 and the peak detecting section 326 detect the respective peaks of the interbeat interval and interpulse interval, and store information such as peak time and peak amplitude in, for example, the RAM for all of the peaks detected.

The peak correcting section 318 calculates the time delay of an electrocardiogram signal in the first signal processing section 310 (the analog filter 312 and the digital filter 314). The peak correcting section 318 corrects the peak of the electrocardiogram signal detected by the peak detecting section 316, on the basis of the calculated time delay of the electrocardiogram signal. Likewise, the peak correcting section 328 calculates the time delay of a photoplethysmogram signal in the second signal processing section 320 (the analog filter 322, the digital filter 324, and the second-derivative processing section 325). The peak correcting section 328 corrects the peak of the photoplethysmogram signal (acceleration plethysmogram signal) detected by the peak detecting section 326, on the basis of the calculated time delay of the photoplethysmogram signal. The corrected peak of the electrocardiogram signal, and the corrected peak of the photoplethysmogram (acceleration plethysmogram) signal are output to the pulse transmission time measuring section 330. If the time delay of an electrocardiogram signal and the time delay of a photoplethysmogram signal can be regarded as substantially equal, the peak correcting section 318 may not necessarily be provided.

Figure 3:
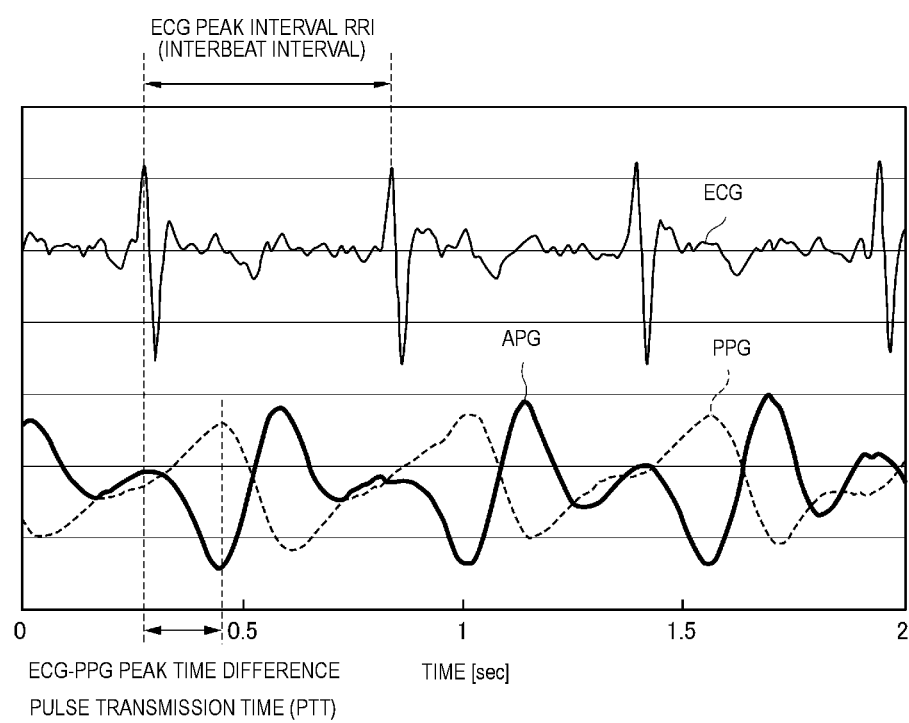
FIG. 3 illustrates an electrocardiogram waveform, a photoplethysmogram waveform, and pulse transmission time.

The pulse transmission time measuring section 330 of the controller calculates pulse transmission time from the interval (time difference) between the R-wave (peak) of the electrocardiogram signal corrected by the peak correcting section 318, and the peak (rising edge) of the photoplethysmogram signal (acceleration plethysmogram) corrected by the peak correcting section 328. That is, the pulse transmission time measuring section 330 functions as pulse transmission time calculating means. FIG. 3 illustrates pulse transmission time calculated from the interval between the R-wave (peak) of an electrocardiogram signal and a peak of a photoplethysmogram signal (acceleration plethysmogram). In FIG. 3, the waveform of the electrocardiogram signal is indicated by a thin solid line, and the waveform of a photoplethysmogram signal is indicated by a dashed line. The waveform of an acceleration plethysmogram is indicated by a thick solid line.

In addition to pulse transmission time, the pulse transmission time measuring section 330 also calculates, for example, heart rate, interbeat interval, and rate of change in interbeat interval from the electrocardiogram signal. Likewise, the pulse transmission time measuring section 330 calculates, for example, pulse rate, interpulse interval, and rate of change in interpulse interval from the photoplethysmogram signal (acceleration plethysmogram). The calculated pulse transmission time, heart rate, interbeat interval, pulse rate, and interpulse interval, the electrocardiogram, the photoplethysmogram, the acceleration plethysmogram, and other such measurement data are output to the pulse transmission time storing section 340, the variation calculating section 350, the biological state estimating section 360, and a display 50.

The pulse transmission time storing section 340, which is implemented by, for example, the backup RAM mentioned above stores measurement data such as pulse transmission time calculated by the pulse transmission time measuring section 330, together with information such as the date and time of measurement. For estimation/evaluation of blood vessel distensibility, in particular, the pulse transmission time storing section 340 stores pulse transmission time measured before the user performs a predetermined action (for example, a step exercise or avascularization) that places a load on the heart. For estimation/evaluation of the quality of sleep (the degree of recovery from fatigue), the pulse transmission time storing section 340 stores pulse transmission time measured before and during sleep. That is, the pulse transmission time storing section 340, which is electronic memory or ROM, functions as pulse transmission time storing means.

The correlation information storing section 341, which is implemented by, for example, the ROM mentioned above, stores correlation information determined in advance on the basis of the relationship between pulse transmission time and biological state. More specifically, the correlation information storing section 341 stores a fatigue table (corresponding to fatigue correlation information, details of which will be given later), an autonomic function table (corresponding to autonomic function correlation information, details of which will be given later), and a blood vessel distensibility table (corresponding to blood vessel distensibility correlation information, details of which will be given later). The fatigue table is determined in advance on the basis of the relationship between pulse transmission time and degree of fatigue. The autonomic function table is determined in advance on the basis of the relationship between pulse transmission time and autonomic function. The blood vessel distensibility table is determined in advance on the basis of the relationship between amount of variation in pulse transmission time before and after a predetermined action that places a load on the heart (for example, a step exercise or avascularization) and blood vessel distensibility. At that time, the correlation information storing section 341 preferably stores correlation information (the fatigue table, the autonomic function table, and the blood vessel distensibility table) representing the relationship between pulse transmission time and biological information (degree of fatigue, autonomic function, and blood vessel distensibility), individually for each age and/or each sex.

Figure 10:
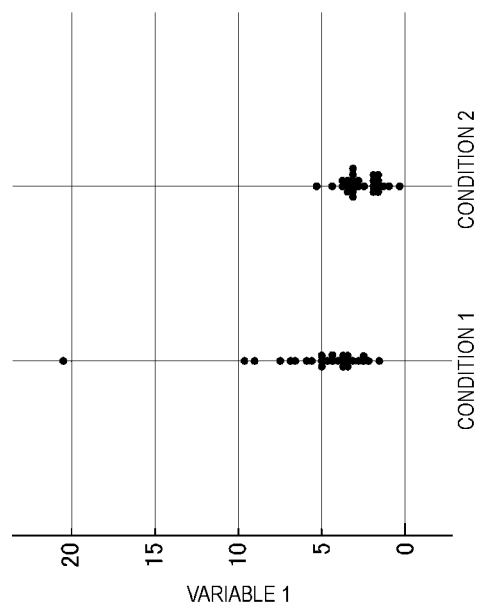
FIG. 10 illustrates association between LF/HF before resting (Variable 1) and LF/HF after resting (Variable 2).
Figure 10:
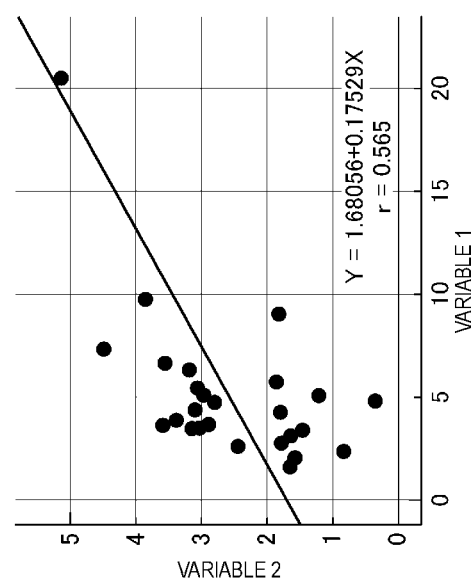
Figure 11:
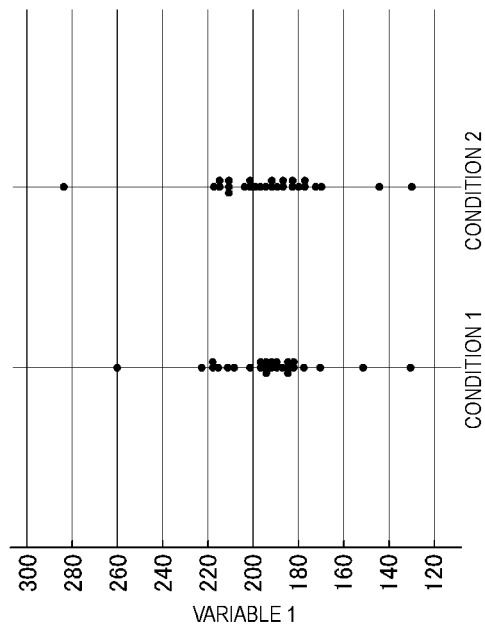
FIG. 11 illustrates association between pulse wave velocity before resting (Variable 1) and pulse wave velocity after resting (Variable 2).
Figure 11:
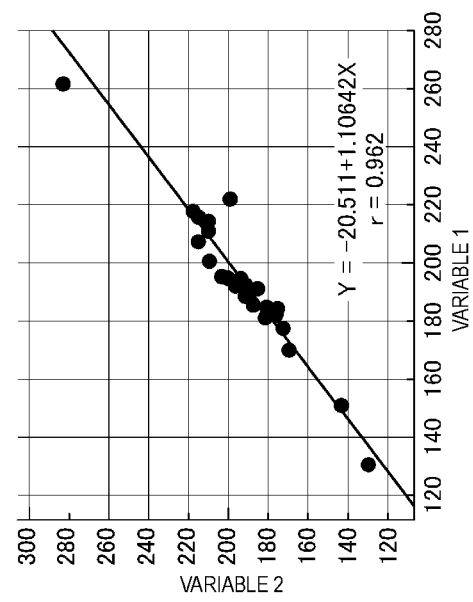

FIGS. 10 and 11 illustrate a comparison between pre-rest and post-rest results when sufficient resting (a five-minute rest) is given to 27 subjects, who were not given a sufficient resting period at the time of autonomic function evaluation and thus had a LF/HF ratio of two or greater (indicating the state of relative hypertension of the sympathetic nervous system). First, FIG. 10 illustrates association between LF/HF before resting (Variable 1) and LF/HF after resting (Variable 2). A significant positive correlation is observed between the pre-rest and post-rest values of LF/HF, which represents the autonomic balance (autonomic function) between the sympathetic and parasympathetic nervous systems. In this regard, the mean LF/HF before resting of 5.176 dropped to 2.588 after resting, indicating a statistically significant decrease.

FIG. 11 illustrates association between pulse wave velocity before resting (Variable 1) and pulse wave velocity after resting (Variable 2). As for the R-a time, which is related to pulse wave velocity, a very strong positive correlation with a correlation coefficient close to 1 is observed between the R-a time before resting and the R-a time after resting. Further, the mean R-a time is almost the same before resting (193.29) and after resting (193.35), and hence no statistically significant difference is observed. This means that evaluation of the R-a time does not require resting prior to measurement. The pulse wave velocity used is calculated by dividing the R-a time (msec), which is the interval between the R-wave of the electrocardiogram and the a-wave of the acceleration plethysmogram, by the length of the arm of the subject.

Dilation and constriction of the blood vessel are regulated by the autonomic nervous system, particularly its sympathetic division. Thus, a correlation exists between pulse transmission time, which is closely related with the dilation and constriction of the blood vessel, and autonomic function, which indicates the balance between the sympathetic nervous system and the parasympathetic nervous system. Accordingly, a correlation equation that defines the relationship between pulse transmission time and index (LF/HF) of autonomic function, or the above-mentioned autonomic function table is created in advance on the basis of an index (LF/HF) of autonomic function calculated from interbeat interval or interpulse interval by frequency analysis, and a measurement of pulse transmission time taken at the same instant of time. The created correlation equation or autonomic function table is then stored in the correlation information storing section 341. In the embodiment, autonomic function is estimated by using the autonomic function table.

Figure 4:
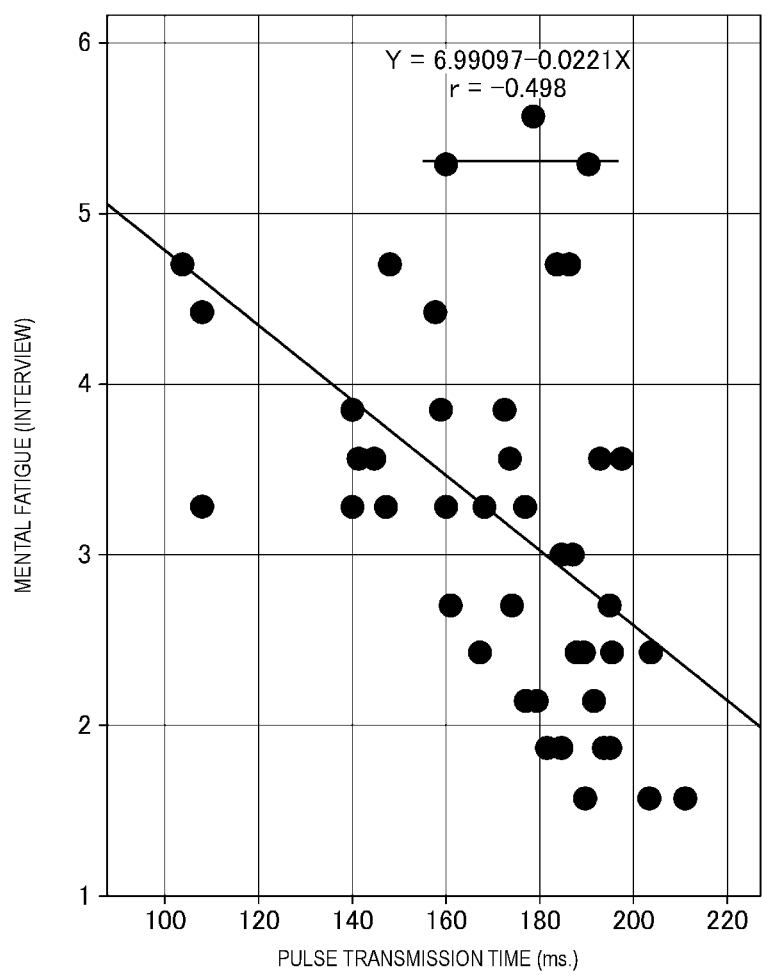
FIG. 4 illustrates an example of correlation data between pulse transmission time and mental fatigue.

Next, an example of correlation data between pulse transmission time and degree of mental fatigue is illustrated in FIG. 4. In the graph illustrated in FIG. 4, the horizontal axis represents pulse transmission time (msec), and the vertical axis represents degree of mental fatigue (results of evaluation by interview). As is evident from FIG. 4, pulse transmission time tends to shorten with increasing degree of mental fatigue. Thus, a correlation equation is obtained from the data illustrated in FIG. 4, and the obtained correlation equation is stored in the correlation information storing section 341. The correlation equation may be a linear approximation. Alternatively, the correlation equation may be, for example, a polynomial approximation or exponential approximation. Instead of a correlation equation, the results of calculation (degree of mental fatigue) obtained in advance with respect to pulse transmission time may be tabulated into a fatigue table for use. As described above, in the embodiment, the fatigue table is stored in the correlation information storing section 341, and used to estimate the degree of fatigue.

Blood vessel distensibility, which is an index of the stiffness or aging of the blood vessel, shows a positive correlation with pulse transmission time. Increasing blood vessel distensibility tends to increase pulse transmission time as well as the amount of variation in pulse transmission time. Accordingly, the correlation between amount of variation in pulse transmission time and blood vessel distensibility is measured in advance, and based on this correlation data, a correlation equation that defines the relationship between amount of variation in pulse transmission time and blood vessel distensibility is determined. The determined correlation equation is then stored in the correlation information storing section 341. Instead of a correlation equation, the results of calculation (blood vessel distensibility) obtained in advance with respect to the amount of variation in pulse transmission time may be tabulated into a blood vessel distensibility table for use. As described above, in the embodiment, the blood vessel distensibility table is stored in the correlation information storing section 341, and used to estimate blood vessel distensibility.

Returning to FIG. 1, based on the pulse transmission time calculated by the pulse transmission time measuring section 330, the variation calculating section 350, which is a component of the controller, calculates the amount of variation in pulse transmission time (and heart rate) before and after a predetermined action that places a load on the heart (for example, a step exercise or avascularization). The amount of variation in pulse transmission time calculated by the variation calculating section 350 is output to the biological state estimating section 360.

The biological state estimating section 360, which is a component of the controller, estimates the user's biological state on the basis of the pulse transmission time obtained by the pulse transmission time measuring section 330 and the correlation information stored in the correlation information storing section 341. That is, the biological state estimating section 360 functions as biological state estimating means.

More specifically, the biological state estimating section 360 estimates the degree of fatigue of the user on the basis of the pulse transmission time and the fatigue table (fatigue correlation information). As described above, the correlation information storing section 341 stores the fatigue table, which defines the relationship between pulse transmission time and degree of fatigue. The biological state estimating section 360 searches the fatigue table by using the measured pulse transmission time to estimate the degree of fatigue.

The biological state estimating section 360 also estimates the autonomic function of the user on the basis of pulse transmission time and the autonomic function table (autonomic function correlation information). As described above, the correlation information storing section 341 stores the autonomic function table that defines the relationship between pulse transmission time and autonomic function. Thus, the biological state estimating section 360 searches the autonomic function table by using the pulse transmission time to estimate autonomic function.

Further, the biological state estimating section 360 estimates the blood vessel distensibility of the user, on the basis of the amount of variation of pulse transmission time calculated by the variation calculating section 350 and the blood vessel distensibility table (blood vessel distensibility correlation information). As described above, the correlation information storing section 341 stores the blood vessel distensibility table that defines the relationship between amount of variation in pulse transmission time and blood vessel distensibility. The biological state estimating section 360 estimates blood vessel distensibility by searching the blood vessel distensibility table stored in the correlation information storing section 341, by using the amount of variation in pulse transmission time calculated by the variation calculating section 350.

The estimated biological state (that is, the degree of fatigue, autonomic function, and/or blood vessel distensibility), and measurement data, such as the calculated pulse transmission time, heart rate, interbeat interval, pulse rate, interpulse interval, electrocardiogram, photoplethysmogram, and acceleration plethysmogram are output to, for example, the display 50. Alternatively, the acquired biological state, and measurement data such as pulse transmission time, heart rate, and pulse rate may be accumulated and stored in, for example, the RAM mentioned above in advance so that after the measurement, these pieces of data is output to, for example, a personal computer (PC) and checked.

The display 50 is implemented by, for example, a liquid crystal display (LCD). The display 50 displays information in real time, such as the estimated biological state, the acquired pulse transmission time, heart rate, pulse rate, and other measurement data (measurement results). The above-mentioned information may be transmitted by a communication section 60 to, for example, a PC, a portable music player having a display, or a smart phone, and displayed on such a device. In that case, preferably, data such as the date and time of measurement is also transmitted in addition to the results of measurement and estimation.

Figure 5:
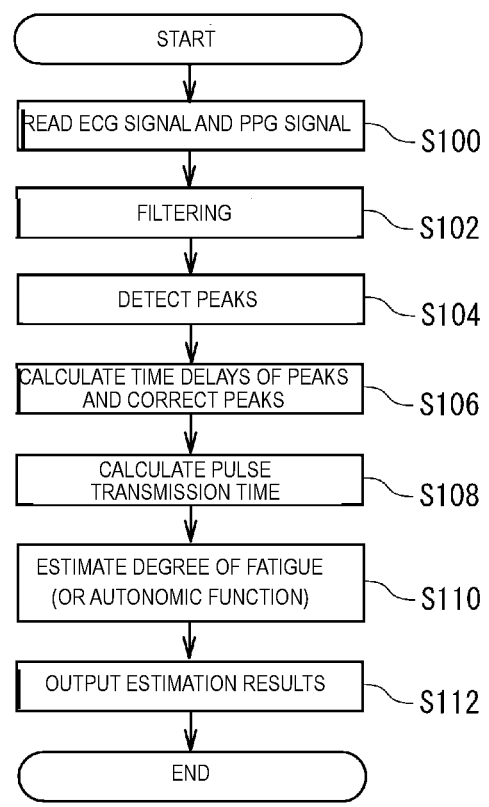
FIG. 5 is a flowchart illustrating a procedure of biological state estimation (fatigue degree/autonomic function) executed by a biological state estimating apparatus according to an embodiment.
Figure 6:
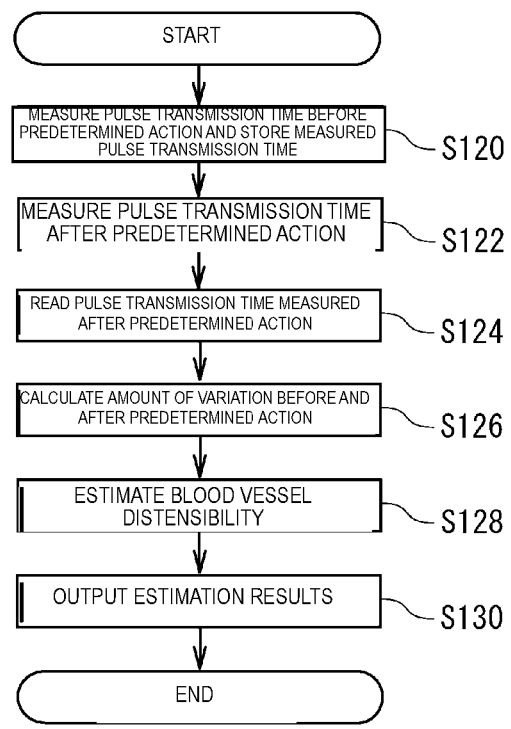
FIG. 6 is a flowchart illustrating a procedure of biological state estimation (blood vessel distensibility) executed by a biological state estimating apparatus according to an embodiment.

Next, operation of the biological state estimating apparatus 1 will be described with reference to FIGS. 5 and 6. FIG. 5 is a flowchart illustrating a procedure of fatigue/autonomic function estimation executed by the biological state estimating apparatus 1. FIG. 6 is a flowchart illustrating a procedure of blood vessel distensibility estimation executed by the biological state estimating apparatus 1. The procedures illustrated in FIGS. 5 and 6 are mainly executed by the signal processing unit 30.

In step S100, an electrocardiogram signal (electrocardiogram waveform) detected by the pair of electrocardiographic electrodes 11 and 12, and a photoplethysmogram signal (photoplethysmogram waveform) detected by the photoplethysmographic sensor 20 are read. Subsequently, in step S102, filtering is applied to the electrocardiogram signal and the photoplethysmogram signal read in step S100. Further, an acceleration plethysmogram is obtained by taking the second derivative of the photoplethysmogram signal.

Next, in step S104, peaks in the electrocardiogram signal and the photoplethysmogram signal (acceleration plethysmogram signal) are detected. Then, peak time, peak amplitude, and other such information are stored for all of the detected peaks.

Subsequently, in step S106, the time delay (shift) of the R-wave peak of the electrocardiogram signal and the time delay (shift) of the peak of the photoplethysmogram signal (acceleration plethysmogram) are determined. Then, the R-wave peak of the electrocardiogram signal and the peak of the photoplethysmogram signal (acceleration plethysmogram) are each corrected on the basis of the determined time delay. Since the method of correcting each peak is as described above, a detailed description in this regard is not provided herein.

Then, in step S108, pulse transmission time is calculated from the corrected peak of the photoplethysmogram signal (acceleration plethysmogram), and the corrected R-wave peak of the electrocardiogram signal.

Next, in step S110, the fatigue table is searched by using the pulse transmission time calculated in step S108, and the degree of fatigue is estimated. Since the fatigue table and the like are as described above, a detailed description in this regard is not provided herein.

In step S110, autonomic function may be estimated instead of the degree of fatigue. In this case, in step S110, the autonomic function table is searched by using the pulse transmission time, and autonomic function is estimated. Since the autonomic function table and the like are as described above, a detailed description in this regard is not provided herein.

Then, in step S112, the degree of fatigue (or autonomic function) estimated in step S110 is output to, for example, the display 50. Thereafter, the processing temporarily exits from this procedure.

Next, a blood vessel distensibility estimation process will be described with reference to FIG. 6. First, in step S120, pulse transmission time is measured prior to, for example, a step exercise, and the measured pulse transmission time is then stored in the pulse transmission time storing section 340.

Then, after the step exercise is performed, pulse transmission time is measured in step S122. Subsequently, in step S124, the pulse transmission time measured prior to the step exercise, which is stored in the pulse transmission time storing section 340, is read.

Next, in step S126, the pulse transmission time after the step exercise measured in step S122, and the pulse transmission time before the step exercise read in step S124 are used to calculate the amount of variation in pulse transmission time before and after the step exercise.

Subsequently, in step S128, the blood vessel distensibility table is searched by using the amount of variation in pulse transmission time calculated in step S126, and blood vessel distensibility is estimated. Since the blood vessel distensibility table and the like are as described above, a detailed description in this regard is not provided herein.

Then, in step S130, the blood vessel distensibility estimated in step S128 is output to, for example, the display 50. Thereafter, the processing temporarily exits from this procedure.

As described above, in the embodiment, the correlation information indicating the relationship between pulse transmission time and biological information is acquired and stored in advance. The biological state of the user is estimated on the basis of the pulse transmission time, which is obtained from the time difference between the peak of an electrocardiogram signal and the peak of a photoplethysmogram signal, and the stored correlation information. That is, the pulse transmission time calculated from the time difference between the peak of an electrocardiogram signal and the peak of a photoplethysmogram signal is used as an index of biological state. As described above, pulse transmission time has a correlation with post-rest LF/HF. That is, a correlation is observed between pulse transmission time and autonomic function. Further, the detected pulse transmission time varies little between when measured at rest and when measured without resting. That is, using pulse transmission time as an index eliminates the need for the user to remain at rest prior to and during the measurement. Data for estimating biological state may be collected for any length of time that is sufficient to obtain pulse transmission time. Hence, in theory, the duration of one beat is sufficient to estimate biological state. Consequently, the measurement time required for biological state evaluation can be shortened in comparison to conventional methods using frequency analysis. As a result, in acquiring biological information (pulse transmission time) for estimating biological state, the user is not required to remain at rest, and further, the biological state of the user can be estimated in a shorter time.

At that time, in the embodiment, grasping the housing 5 allows acquisition of an electrocardiogram signal between both hands as well as a photoplethysmogram signal, that is, acquisition of pulse transmission time. Thus, the biological state can be estimated and evaluated by the user's simple action of grasping the housing 5.

In the embodiment, the correlation information indicating the relationship between pulse transmission time and biological information is acquired and stored individually for, for example, each age or each sex. This allows for more accurate estimation/evaluation of biological state by taking differences due to, for example, age or sex into account.

In particular, the fatigue table (fatigue correlation information) is stored in the embodiment, which is determined in advance on the basis of the relationship between pulse transmission time and degree of fatigue. Thus, by measuring the pulse transmission time of the user, the degree of fatigue can be estimated and evaluated by using the measured pulse transmission time as an index.

Further, the autonomic function table (autonomic function correlation information) is stored in the embodiment, which is determined in advance on the basis of the relationship between pulse transmission time and autonomic function. Thus, by measuring the pulse transmission time of the user, autonomic function can be estimated and evaluated by using the measured pulse transmission time as an index.

Furthermore, the blood vessel distensibility table (blood vessel distensibility correlation information) is stored in the embodiment, which is determined in advance on the basis of the relationship between amount of variation in pulse transmission time before and after a predetermined action that places a load on the heart (for example, a step exercise or avascularization), and distensibility of the blood vessel. Thus, by measuring the pulse transmission time of the user, the distensibility of the blood vessel can be estimated and evaluated by using the measured pulse transmission time as an index.

(First Modification)

Figure 7:
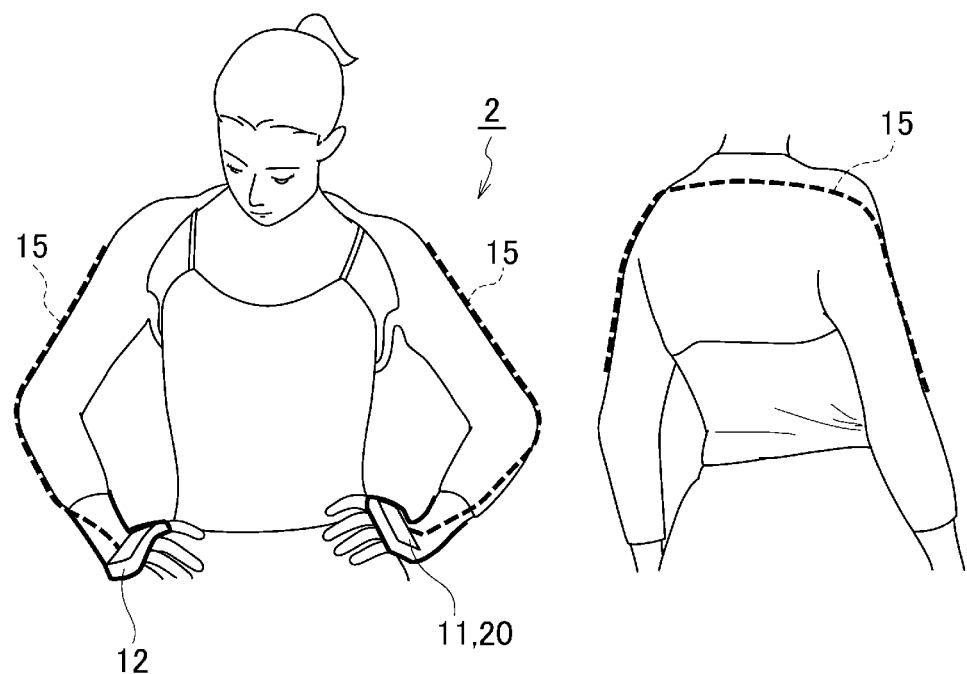
FIG. 7 illustrates a general configuration of a biological state estimating apparatus according to a first modification.

In the above embodiment, the biological state estimating apparatus is of a portable type with components such as the first electrocardiographic electrode 11, the second electrocardiographic electrode 12, and the photoplethysmographic sensor 20 attached to the housing 5. Alternatively, for example, the biological state estimating apparatus may be of a type that can be worn on the body (that is, a wearable type) as illustrated in FIG. 7. This allows for easier measurement of pulse transmission time during sleep, for example.

As illustrated in FIG. 7, a biological state estimating apparatus 2 according to a first modification has the first electrocardiographic electrode 11, the second electrocardiographic electrode 12, the photoplethysmographic sensor 20, and other components that are attached to a wearable piece of fabric running continuously from the tip of each arm to the shoulder and the back of the user. The piece of fabric may not be provided for the trunk portion of the body that is not required for measurement or wiring.

The biological state estimating apparatus 2 is attached in such a way that when worn, the electrocardiographic electrode 11 of the pair of electrocardiographic electrodes 11 and 12 is in contact with a site (the back of the hand in the first modification) between the fingertip and the shoulder of one arm (for example, the left arm), and the other electrocardiographic electrode 12, is in contact with a site (the back of the hand in the first modification) between the fingertip and the shoulder of the other arm (for example, the right arm). A wiring cable 15, which is attached to the electrocardiographic electrode 11 and/or the other electrocardiographic electrode 12, is attached to the piece of fabric so as to run along the user's body surface. The photoplethysmographic sensor 20 is preferably attached in contact with a site (the back of a hand in the first modification) between the fingertip of the hand and the shoulder.

Figure 8:
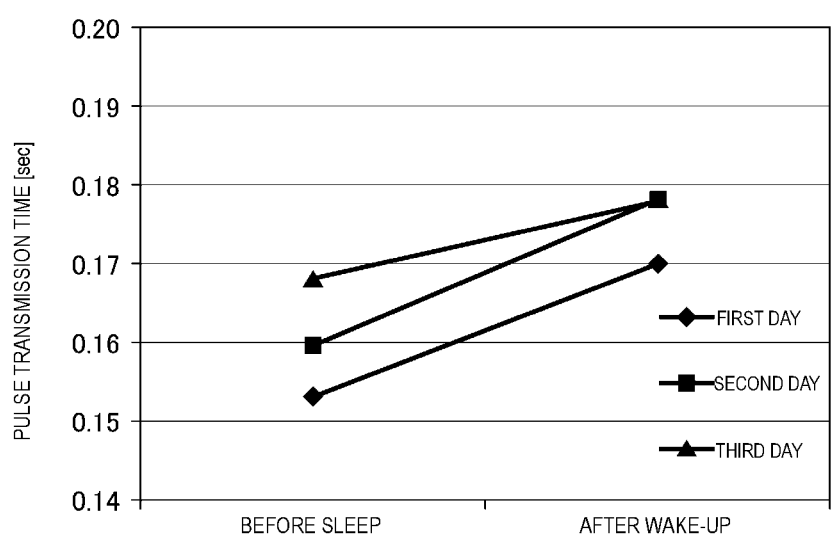
FIG. 8 illustrates an example of how pulse transmission time changes before and after sleep.

Pulse transmission time varies depending on the time of day. Generally, as illustrated in FIG. 8, pulse transmission time tends to be relatively long in the morning and relatively short at night. This suggests a shorter pulse transmission time at night when fatigue is elevated than in the morning when fatigue is comparatively less. The decreased pulse transmission time increases with recovery from fatigue by sleep. Thus, the quality of sleep (the degree of recovery from fatigue) is estimated from the values of pulse transmission time before and after sleep.

Accordingly, in the first modification, a sleep state table (corresponding to sleep state correlation information) is stored in the correlation information storing section 341 in advance to estimate the quality of sleep. The sleep state table is determined in advance on the basis of the relationship between pulse transmission time before sleep (falling asleep), pulse transmission time after sleep (after waking up), and quality of sleep (degree of recovery from fatigue).

The biological state estimating section 360 estimates the quality of sleep (the degree of recovery from fatigue) on the basis of the pulse transmission time before sleep (falling asleep) determined by the pulse transmission time measuring section 330 and stored in the pulse transmission time storing section 340, pulse transmission time after sleep (after waking up) determined by the pulse transmission time measuring section 330, and the sleep state table. The first modification is otherwise identical or similar in configuration to the above-mentioned embodiment (the biological state estimating apparatus 1), and thus a detailed description in this regard is not provided herein.

Figure 9:
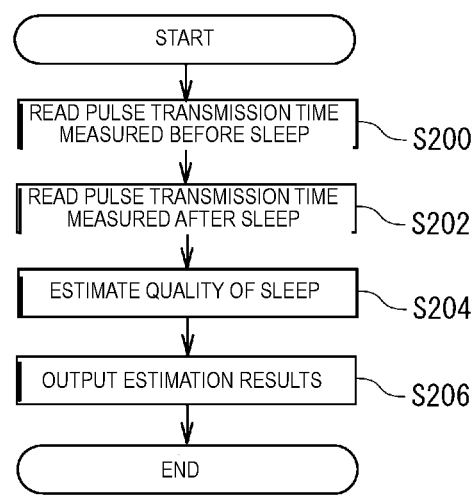
FIG. 9 is a flowchart illustrating a procedure of biological state estimation (quality of sleep) executed by the biological state estimating apparatus according to the first modification.

Next, operation of the biological state estimating apparatus 2 will be described with reference to FIG. 9. FIG. 9 is a flowchart illustrating a procedure of sleep quality estimation executed by the biological state estimating apparatus 2. The procedure illustrated in FIG. 9 is mainly executed by the signal processing unit 30.

In step S200, a stored pulse transmission time before sleep is read. Subsequently, in step S202, a measured pulse transmission time after sleep is read.

Next, in step S204, the sleep state table is searched by using the pulse transmission time before sleep read in step S200, and the pulse transmission time after sleep read in step S202, and the quality of sleep (the degree of recovery from fatigue) is estimated.

Then, in step S206, the quality of sleep estimated in step S204 is output to, for example, the display 50. Thereafter, the processing temporarily exits from this procedure.

The first modification allows pulse transmission time to be measured with the pair of electrocardiographic electrodes 11 and 12 and the photoplethysmographic sensor 20 placed on the body of the user. Thus, as the user sleeps while wearing these components on the body, pulse transmission time during sleep is acquired to enable estimation/evaluation of the quality of sleep (the degree of recovery from fatigue). It is also possible to measure pulse transmission time during active daytime hours to sequentially estimate/evaluate the biological state (for example, the degree of fatigue).

In this case, in particular, the sleep state table is stored, which is determined in advance on the basis of the relationship between pulse transmission time before and after sleep and state of sleep. Thus, by measuring the pulse transmission time of the user before and after sleep and using the measured pulse transmission time as an index, the quality of sleep can be estimated and evaluated as a biological state.

This modification enables continuous measurement of pulse transmission time while the user is asleep, thus allowing estimation of REM sleep and non-REM sleep as well as estimation of, for example, sleep efficiency (the ratio of the effective sleeping time for recovery from fatigue to the time spent in bed) and the number of arousals during sleep at night at the same time.

(Second Modification)

The acquisition of pulse transmission time, and the estimation of biological state (such as the degree of fatigue, autonomic function, blood vessel distensibility, or the quality of sleep) may be started or ended automatically. Guidance may be given by voice or an image at the time of automatically starting and/or ending the estimation.

In a second modification, for example, the biological state estimating section 360 automatically starts estimation of the biological state upon satisfaction of at least one of the following conditions: detection of the user's contact; acquisition of an electrocardiogram signal and a photoplethysmogram signal over a predetermined number of beats (for example, several beats); and payment of a consideration.

In the second modification, for example, the biological state estimating section 360 automatically ends estimation of biological state upon acquisition of an electrocardiogram signal and a photoplethysmogram signal over a predetermined number of beats (for example, 30 beats), and/or upon elapse of a predetermined time (for example, 30 seconds) after estimation of biological state is started.

Further, in the second modification, guidance by voice and/or an image is presented by, for example, a speaker 70 or the display 50 at the time of automatically starting and/or ending estimation of the biological state. That is, the speaker 70 and the display 50 correspond to presenting unit.

In the second modification, estimation of biological state is automatically started, eliminating the need for an action to start measurement/detection. This eliminates body motion noise resulting from such a starting action, and enables measurement/detection under relative resting conditions.

In the second modification, pulse transmission time measurement/biological state estimation is automatically ended upon its completion. This enables easier measurement of pulse transmission time to estimate biological state.

Further, the second modification makes it possible to inform the user of the status of measurement, such as start of measurement/estimation or end of measurement/estimation.

While an embodiment of the present invention has been described above, the present invention is not limited to the above-mentioned embodiment but can be practiced with various modifications. For example, although the above embodiment uses the fatigue table to estimate the degree of fatigue, the degree of fatigue may be estimated by computation on the basis of a correlation equation. Likewise, although the autonomic function table is used to estimate autonomic function, autonomic function may be estimated by computation on the basis of a correlation equation. Similarly, the quality of sleep, and the distensibility of the blood vessel may be also estimated by computation.

In the above embodiment, the user's biological state is estimated on the basis of correlation information (such as the fatigue table) stored in advance. In estimating the biological state (such as the degree of fatigue) on the basis of correlation information, the correlation information may be corrected on the basis of, for example, heart rate, blood pressure, and/or the distance between the site of detection of the photoplethysmogram signal and the heart.

In the above embodiment, the degree of fatigue is estimated by searching the fatigue table on the basis of a measured pulse transmission time. At this time, the degree of fatigue may be estimated in a comprehensive manner by further taking the estimated autonomic function, quality of sleep, and/or blood vessel distensibility into consideration.

In the above embodiment, the degree of fatigue is estimated on the basis of pulse transmission time. At this time, the degree of fatigue may be estimated in a comprehensive manner by further taking the analysis results of autonomic function based on interbeat interval or interpulse interval into consideration. This allows for comprehensive estimation of physical fatigue and mental fatigue, which differ in their cause and symptoms.

In the above embodiment, the distensibility of the blood vessel is estimated on the basis of the amount of variation in pulse transmission time. At this time, the distensibility of the blood vessel may be estimated in a comprehensive manner by further taking the peak height ratio of the waveform of an acceleration plethysmogram into consideration. This allows the distensibility of the blood vessel to be estimated with improved accuracy.

In the above embodiment, the first and second electrocardiographic electrodes 11 and 12, and the photoplethysmographic sensor 20 are disposed on the upper surface of the housing 5. Alternatively, for example, these components may be disposed in locations on the back surface of the housing 5 with which the middle finger or other body part of the user comes into contact.

As described above, acquired measurement data such as a heartbeat signal and a pulse signal may be output to and displayed on, for example, a PC, a portable music player having a display, or a smart phone. In that case, estimation of the biological state may be performed on the PC or smart phone. Further, data may be transmitted to a server and processed on the server. In this case, data such as the correlation information mentioned above is stored on the PC, smart phone, or server.

In the first modification mentioned above, the quality of sleep is estimated from the values of pulse transmission time before and after sleep. Alternatively, the quality of sleep may be estimated by storing a sleep state table (corresponding to sleep state correlation information) in the correlation information storing section 341, which is determined in advance on the basis of the relationship between variation of pulse transmission time during sleep and quality of sleep (degree of recovery from fatigue). In that case, the pulse transmission time storing section 340 stores variation of pulse transmission time during sleep, and the biological state estimating section 360 estimates the quality of sleep (the degree of recovery from fatigue) on the basis of the variation of pulse transmission time during sleep stored in the pulse transmission time storing section 340 as well as the sleep state table. In this case, the user's sleep state (the quality of sleep, that is, the degree of recovery from fatigue) can be estimated and evaluated by measuring variation of pulse transmission time of the user during sleep.

REFERENCE SIGNS LIST 1, 2 biological state estimating apparatus
5 housing
11 first electrocardiographic electrode
12 second electrocardiographic electrode
15 wiring cable
20 photoplethysmographic sensor
21 light-emitting element
22 light-receiving element
30 signal processing unit
300 arithmetic processing device
310 first signal processing section
320 second signal processing section
311, 321 amplifying section
312, 322 analog filter
313, 323 A/D converter
314, 324 digital filter
325 second-derivative processing section
316, 326 peak detecting section
318, 328 peak correcting section
330 pulse transmission time measuring section
340 pulse transmission time storing section
341 correlation information storing section
350 variation calculating section
360 biological state estimating section
50 display
60 communication section
70 speaker

The invention claimed is:

1. A biological state estimating apparatus comprising:
a pair of non-invasive electrocardiographic electrodes configured to detect an electrocardiogram signal of a user without implanting the electrocardiographic electrodes in the user;
a non-invasive photoplethysmographic sensor configured to detect a photoplethysmogram signal, the non-invasive photoplethysmographic sensor having a light-emitting element and a light-receiving element;
electronic memory storing a plurality of sleep state correlation information that indicates a relationship between pulse transmission times and a state of sleep and that is predetermined based on a relationship between pulse transmission times before sleep, pulse transmission times after sleep, and a state of sleep; and
a controller configured to:
detect a peak of the electrocardiogram signal,
detect a peak of the photoplethysmogram signal,
calculate a pulse transmission time based on a time difference between the respective peaks of the photoplethysmogram signal and the electrocardiogram signal, and
estimate a state of sleep of the user based on a calculated pulse transmission time before sleep of the user, a calculated pulse transmission time after sleep of the user, and the plurality of sleep state correlation information stored in the electronic memory.

2. The biological state estimating apparatus according to claim 1,
wherein the controller is further configured to calculate an amount of variation in a calculated pulse transmission time before and after a predetermined action that places a load on a heart,
wherein the electronic memory further stores blood vessel distensibility correlation information that is predetermined based on a relationship between an amount of variation in pulse transmission time before and after the predetermined action and blood vessel distensibility, and
wherein the controller is further configured to estimate blood vessel distensibility of the user based on an amount of variation in a calculated pulse transmission time and the blood vessel distensibility correlation information.

3. The biological state estimating apparatus according to claim 1,
wherein the non-invasive electrocardiographic electrodes are attached to a housing at a location on the housing such that when the user grasps the housing with left and right hands, one of the left and right hands is in contact with a first of the electrocardiographic electrodes and another of the left and right hands is in contact with a second of the electrocardiographic electrodes, and
wherein the non-invasive photoplethysmographic sensor is attached to the housing at a location such that when the user grasps the housing with the left and right hands, the non-invasive photoplethysmographic sensor is in contact with one of the left and right hands of the user.

4. The biological state estimating apparatus according to claim 1,
wherein one of the non-invasive electrocardiographic electrodes is configured to be in contact with the user between a fingertip and a shoulder on one arm of the user, another of the non-invasive electrocardiographic electrodes is configured to be in contact with the user between a fingertip and a shoulder on another arm of the user, and a wiring cable connected to the non-invasive electrocardiographic electrodes is configured to be routed along a surface of a body of the user, and
wherein the non-invasive photoplethysmographic sensor is configured to be in contact with between the fingertip and the shoulder on one of the one arm and the another arm of the user.

5. The biological state estimating apparatus according to claim 1, wherein the electronic memory stores the plurality of sleep state correlation information indicative of the relationship between pulse transmission times and the state of sleep, individually for at least one of each age and each sex.

6. The biological state estimating apparatus according to claim 1, wherein the controller automatically starts estimating the state of sleep of the user upon satisfaction of at least one condition including detecting contact of the user with the biological state estimating apparatus, acquiring the electrocardiogram signal and the photoplethysmogram signal over a predetermined number of beats, and payment of a consideration.

7. The biological state estimating apparatus according to claim 6, wherein the controller is further configured to automatically stop estimating the state of sleep of the user upon satisfaction of at least one condition including acquisition of the electrocardiogram signal and the photoplethysmogram signal over a predetermined number of beats, and lapsing of a predetermined time after the estimating of the state of sleep is started.

8. The biological state estimating apparatus according to claim 7, further comprising a presenting unit configured to present information relating to the estimate state of sleep of the user by at least one of guidance by voice and an image, at a time of automatically starting the estimating of the state of sleep and automatically ending the estimating of the state of sleep.

9. The biological state estimating apparatus according to claim 1, wherein the electronic memory stores the plurality of sleep state correlation information in a table of biological information that is predetermined based on the relationship between the pulse transmission times and the state of sleep.

10. A biological state estimating apparatus comprising:
a pair of non-invasive electrocardiographic electrodes configured to detect an electrocardiogram signal of a user without implanting the electrocardiographic electrodes in the user;
a non-invasive photoplethysmographic sensor configured to detect a photoplethysmogram signal, the non-invasive photoplethysmographic sensor having a light-emitting element and a light-receiving element;
electronic memory storing a plurality of sleep state correlation information that indicates a relationship between pulse transmission times and a state of sleep and that is predetermined based on a relationship between a variation of pulse transmission times during sleep and a state of sleep; and
a controller configured to:
detect a peak of the electrocardiogram signal,
detect a peak of the photoplethysmogram signal,
calculate a pulse transmission time based on a time difference between the respective peaks of the photoplethysmogram signal and the electrocardiogram signal, and
estimate a state of sleep of the user based on a variation of the calculated pulse transmission time during sleep of the user and the sleep state correlation information stored in the electronic memory.

11. A method for estimating a biological state of a user, the method comprising:
detecting an electrocardiogram signal of the user by a pair of non-invasive electrocardiographic electrodes without implanting the electrocardiographic electrodes in the user;
detecting a photoplethysmogram signal of the user by a non-invasive photoplethysmographic sensor having a light-emitting element and a light-receiving element;
storing, by electronic memory, a plurality of sleep state correlation information that indicates a relationship between pulse transmission times and a state of sleep and that is predetermined based on a relationship between pulse transmission times before sleep, pulse transmission times after sleep, and a state of sleep;
detecting a peak of the electrocardiogram signal;
detecting a peak of the photoplethysmogram signal;
calculating a pulse transmission time based on a time difference between the respective peaks of the photoplethysmogram signal and the electrocardiogram signal;
storing, by the electronic memory, the calculated pulse transmission time; and
estimating a state of sleep of the user based on a calculated pulse transmission time before sleep of the user, a calculated pulse transmission time after sleep of the user, and the plurality of sleep state correlation information stored in the electronic memory.

12. The method for estimating the biological state of the user according to claim 11, further comprising:
storing, by the electronic memory, a variation of the calculated pulse transmission time and the sleep state correlation information that is predetermined based on a relationship between variation of pulse transmission times during sleep and the state of sleep; and
estimating the state of sleep of the user based on a variation of a calculated pulse transmission time during the sleep of the user and the sleep state correlation information.

13. The method for estimating the biological state of the user according to claim 11, further comprising:

calculating an amount of variation in a calculated pulse transmission time before and after a predetermined action that places a load on a heart;

storing, by the electronic memory, blood vessel distensibility correlation information that is predetermined based on a relationship between an amount of variation in pulse transmission time before and after the predetermined action and blood vessel distensibility; and estimating blood vessel distensibility of the user based on an amount of variation in a calculated pulse transmission time and the blood vessel distensibility correlation information.

14. The method for estimating the biological state of the user according to claim 11, further comprising storing, by the electronic memory, the plurality of sleep state correlation information indicative of the relationship between pulse transmission times and state of sleep, individually for at least one of each age and each sex.

15. The method for estimating the biological state of the user according to claim 11, further comprising automatically starting estimating the state of sleep of the user upon satisfaction of at least one condition including detecting contact of the user with at least one of the non-invasive electrocardiographic electrodes and the non-invasive photoplethysmographic sensor, acquiring the electrocardiogram signal and the photoplethysmogram signal over a predetermined number of beats, and payment of a consideration.

* * * * *